US011621073B2

(12) United States Patent
Taub et al.

(10) Patent No.: US 11,621,073 B2
(45) Date of Patent: Apr. 4, 2023

(54) CLOSED LOOP CONTROL SYSTEM INTERFACE AND METHODS

(71) Applicant: Abbott Diabetes Care Inc., Alameda, CA (US)

(72) Inventors: Marc Barry Taub, Mountain View, CA (US); Daniel Milfred Bernstein, El Granada, CA (US); Gary Alan Hayter, Oakland, CA (US); Mark Kent Sloan, Redwood City, CA (US); Glenn Howard Berman, Alameda, CA (US); Saeed Nekoomaram, San Mateo, CA (US)

(73) Assignee: Abbott Diabetes Care Inc., Alameda, CA (US)

(*) Notice: Subject to any disclaimer, the term of this patent is extended or adjusted under 35 U.S.C. 154(b) by 474 days.

(21) Appl. No.: 16/451,676

(22) Filed: Jun. 25, 2019

(65) Prior Publication Data

US 2019/0381244 A1     Dec. 19, 2019

Related U.S. Application Data

(63) Continuation of application No. 14/529,026, filed on Oct. 30, 2014, now Pat. No. 10,328,201, which is a
(Continued)

(51) Int. Cl.
    *G16H 40/67*      (2018.01)
    *A61B 5/00*      (2006.01)
(Continued)

(52) U.S. Cl.
    CPC ........... *G16H 40/67* (2018.01); *A61B 5/0031* (2013.01); *A61B 5/14532* (2013.01);
(Continued)

(58) Field of Classification Search
    CPC ........ A61M 5/1723; A61M 2005/1726; A61M 2205/3303; A61M 2230/201;
(Continued)

(56) References Cited

U.S. PATENT DOCUMENTS 3,581,062 A    5/1971   Aston
3,926,760 A   12/1975   Allen et al.
(Continued)

FOREIGN PATENT DOCUMENTS

DE          4401400      7/1995
EP           0098592      1/1984
(Continued)

OTHER PUBLICATIONS

Armour, J. C., et al., "Application of Chronic Intravascular Blood Glucose Sensor in Dogs", *Diabetes*, vol. 39, 1990, pp. 1519-1526.
(Continued)

*Primary Examiner* — Kami A Bosworth
(74) *Attorney, Agent, or Firm* — Sterne, Kessler, Goldstein & Fox P.L.L.C.

(57) ABSTRACT

A method of providing treatment for a medical condition includes storing a plurality of closed loop control algorithms in memory accessible by the control unit and receiving. A control unit receives analyte data from an analyte sensor in communication with the control unit. The control unit controls a medication delivery device in accordance with the first closed loop control algorithm based on the analyte data. The control unit causes the medication delivery device to be controlled in accordance with the second closed loop control algorithm instead of the first closed loop control algorithm, and controlling the medication delivery device in accordance with the second closed loop control algorithm. The
(Continued)

control unit is configured to transmit one or more closed loop control operations to control the medication delivery device.

21 Claims, 7 Drawing Sheets

Related U.S. Application Data continuation of application No. 12/503,022, filed on Jul. 14, 2009, now Pat. No. 8,876,755.

(60) Provisional application No. 61/080,677, filed on Jul. 14, 2008.

(51) Int. Cl.
*A61B 5/145* (2006.01)
*A61M 5/172* (2006.01)
*G16H 20/17* (2018.01)

(52) U.S. Cl.
CPC ........ *A61B 5/14546* (2013.01); *A61B 5/4839* (2013.01); *A61M 5/1723* (2013.01); *G16H 20/17* (2018.01); *A61M 2230/201* (2013.01)

(58) Field of Classification Search
CPC ...... A61M 2205/35; A61M 2205/3507; A61M 2205/3523; A61M 2205/3546–3592; A61B 5/4839; G16H 20/17; G16H 40/60; G16H 40/63; G16H 40/67
See application file for complete search history.

(56) References Cited

U.S. PATENT DOCUMENTS

| | | |
|---|---|---|
| 3,949,388 A | 4/1976 | Fuller |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,425,920 A | 1/1984 | Bourland et al. |
| 4,441,968 A | 4/1984 | Emmer et al. |
| 4,464,170 A | 8/1984 | Clemens et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,671,288 A | 6/1987 | Gough |
| 4,703,756 A | 11/1987 | Gough et al. |
| 4,711,245 A | 12/1987 | Higgins et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,145,381 A | 9/1992 | Volz |
| 5,165,407 A | 11/1992 | Wilson et al. |
| 5,202,261 A | 4/1993 | Musho et al. |
| 5,210,778 A | 5/1993 | Massart |
| 5,228,449 A | 7/1993 | Christ et al. |
| 5,231,988 A | 8/1993 | Wernicke et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,715 A | 6/1994 | Berg |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,410,326 A | 4/1995 | Goldstein |
| 5,411,647 A | 5/1995 | Johnson et al. |
| 5,431,160 A | 7/1995 | Wilkins |
| 5,431,921 A | 7/1995 | Thombre |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,543,326 A | 8/1996 | Heller et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,324 A | 5/1997 | Sarbach |
| 5,628,890 A | 5/1997 | Nigel et al. |
| 5,653,239 A | 8/1997 | Pompei et al. |
| 5,660,163 A | 8/1997 | Schulman et al. |
| 5,665,222 A | 9/1997 | Heller et al. |
| 5,711,001 A | 1/1998 | Bussan et al. |
| 5,711,861 A | 1/1998 | Ward et al. |
| 5,735,285 A | 4/1998 | Albert et al. |
| 5,772,586 A | 6/1998 | Heinonen et al. |
| 5,791,344 A | 8/1998 | Schulman et al. |
| 5,797,940 A | 8/1998 | Mawhirt et al. |
| 5,814,020 A | 9/1998 | Gross |
| 5,820,551 A | 10/1998 | Hill et al. |
| 5,822,715 A | 10/1998 | Worthington et al. |
| 5,833,603 A | 11/1998 | Kovacs et al. |
| 5,842,189 A | 11/1998 | Keeler et al. |
| 5,858,001 A | 1/1999 | Tsals et al. |
| 5,899,855 A | 5/1999 | Brown |
| 5,918,603 A | 7/1999 | Brown |

(56) References Cited

U.S. PATENT DOCUMENTS

| | | |
|---|---|---|
| 5,925,021 A | 7/1999 | Castellano et al. |
| 5,931,814 A | 8/1999 | Gross et al. |
| 5,942,979 A | 8/1999 | Luppino |
| 5,954,643 A | 9/1999 | Van Antwerp et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,980,708 A | 11/1999 | Champagne et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,071,391 A | 6/2000 | Gotoh et al. |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,144,837 A | 11/2000 | Quy |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,186,982 B1 | 2/2001 | Gross et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,259,937 B1 | 7/2001 | Schulman et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,299,347 B1 | 10/2001 | Pompei |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,322,801 B1 | 11/2001 | Lorenzi et al. |
| 6,329,161 B1 | 12/2001 | Heller et al. |
| 6,331,244 B1 | 12/2001 | Lewis et al. |
| 6,338,790 B1 | 1/2002 | Feldman et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,368,141 B1 | 4/2002 | Van Antwerp et al. |
| 6,377,828 B1 | 4/2002 | Chaiken et al. |
| 6,377,894 B1 | 4/2002 | Deweese et al. |
| 6,379,301 B1 | 4/2002 | Worthington et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,445,374 B2 | 9/2002 | Albert et al. |
| 6,461,496 B1 | 10/2002 | Feldman et al. |
| 6,471,689 B1 | 10/2002 | Joseph et al. |
| 6,478,736 B1 | 11/2002 | Mault |
| 6,482,176 B1 | 11/2002 | Wich |
| 6,484,046 B1 | 11/2002 | Say et al. |
| 6,493,069 B1 | 12/2002 | Nagashimada et al. |
| 6,498,043 B1 | 12/2002 | Schulman et al. |
| 6,503,381 B1 | 1/2003 | Gotoh et al. |
| 6,512,939 B1 | 1/2003 | Colvin et al. |
| 6,514,460 B1 | 2/2003 | Fendrock |
| 6,514,689 B2 | 2/2003 | Han et al. |
| 6,514,718 B2 | 2/2003 | Heller et al. |
| 6,522,927 B1 | 2/2003 | Bishay et al. |
| 6,540,891 B1 | 4/2003 | Stewart et al. |
| 6,546,268 B1 | 4/2003 | Ishikawa et al. |
| 6,551,494 B1 | 4/2003 | Heller et al. |
| 6,554,798 B1 | 4/2003 | Mann et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulsen et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,730,200 B1 | 5/2004 | Stewart et al. |
| 6,733,446 B2 | 5/2004 | Lebel et al. |
| 6,736,957 B1 | 5/2004 | Forrow et al. |
| 6,740,075 B2 | 5/2004 | Lebel et al. |
| 6,740,518 B1 | 5/2004 | Duong et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,837,988 B2 | 1/2005 | Leong et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,892,085 B2 | 5/2005 | McIvor et al. |

(56) References Cited

U.S. PATENT DOCUMENTS

| | | |
|---|---|---|
| 6,893,545 B2 | 5/2005 | Gotoh et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,971,999 B2 | 12/2005 | Py et al. |
| 6,974,437 B2 | 12/2005 | Lebel et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,016,713 B2 | 3/2006 | Gardner et al. |
| 7,024,245 B2 | 4/2006 | Lebel et al. |
| 7,025,425 B2 | 4/2006 | Kovatchev et al. |
| 7,027,848 B2 | 4/2006 | Robinson et al. |
| 7,027,931 B1 | 4/2006 | Jones et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,073,246 B2 | 7/2006 | Bhullar et al. |
| 7,074,307 B2 | 7/2006 | Simpson et al. |
| 7,081,195 B2 | 7/2006 | Simpson et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,167,818 B2 | 1/2007 | Brown |
| 7,171,274 B2 | 1/2007 | Starkweather et al. |
| 7,174,199 B2 | 2/2007 | Berner et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,291,497 B2 | 11/2007 | Holmes et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,386,937 B2 | 6/2008 | Bhullar et al. |
| 7,404,796 B2 | 7/2008 | Ginsberg |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,474,992 B2 | 1/2009 | Ariyur |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,630,748 B2 | 12/2009 | Budiman |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,766,829 B2 | 8/2010 | Sloan et al. |
| 7,768,386 B2 | 8/2010 | Hayter et al. |
| 7,768,387 B2 | 8/2010 | Fennell et al. |
| 7,774,145 B2 | 8/2010 | Bruaker et al. |
| 7,775,444 B2 | 8/2010 | DeRocco et al. |
| 7,778,680 B2 | 8/2010 | Goode, Jr. et al. |
| 7,778,795 B2 | 8/2010 | Fukushima et al. |
| 7,811,231 B2 | 10/2010 | Jin et al. |
| 7,813,809 B2 | 10/2010 | Strother et al. |
| 7,826,382 B2 | 11/2010 | Sicurello et al. |
| 7,826,981 B2 | 11/2010 | Goode, Jr. et al. |
| 7,866,026 B1 | 1/2011 | Wang et al. |
| 7,882,611 B2 | 2/2011 | Shah et al. |
| 7,889,069 B2 | 2/2011 | Fifolt et al. |
| 7,899,545 B2 | 3/2011 | John |
| 7,905,833 B2 | 3/2011 | Brister et al. |
| 7,911,010 B2 | 3/2011 | Stetter |
| 7,914,450 B2 | 3/2011 | Goode, Jr. et al. |
| 7,920,906 B2 | 4/2011 | Goode et al. |
| 7,928,850 B2 | 4/2011 | Hayter et al. |
| 7,941,200 B2 | 5/2011 | Weinert et al. |
| 7,946,985 B2 | 5/2011 | Mastrototaro et al. |
| 7,954,385 B2 | 6/2011 | Raisanen |
| 7,972,296 B2 | 7/2011 | Braig et al. |
| 7,974,672 B2 | 7/2011 | Shults et al. |
| 7,976,466 B2 | 7/2011 | Ward et al. |
| 7,978,063 B2 | 7/2011 | Baldus et al. |
| 8,010,174 B2 | 8/2011 | Goode et al. |
| 8,192,394 B2 | 6/2012 | Estes et al. |
| 8,216,138 B1 | 7/2012 | McGarraugh et al. |
| 8,239,166 B2 | 8/2012 | Hayter et al. |
| 8,282,549 B2 | 10/2012 | Brauker et al. |
| 2001/0031931 A1 | 10/2001 | Cunningham et al. |
| 2001/0037366 A1 | 11/2001 | Webb et al. |
| 2002/0019022 A1 | 2/2002 | Dunn et al. |
| 2002/0032374 A1 | 3/2002 | Holker et al. |
| 2002/0042090 A1 | 4/2002 | Heller et al. |
| 2002/0050250 A1 | 5/2002 | Peterson et al. |
| 2002/0052618 A1 | 5/2002 | Haar et al. |
| 2002/0054320 A1 | 5/2002 | Ogino |
| 2002/0055711 A1 | 5/2002 | Lavi et al. |
| 2002/0068860 A1 | 6/2002 | Clark |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0147135 A1 | 10/2002 | Schnell |
| 2002/0161288 A1 | 10/2002 | Shin et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0060692 A1 | 3/2003 | Ruchti et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |

(56) References Cited

U.S. PATENT DOCUMENTS

| | | |
|---|---|---|
| 2003/0114897 A1 | 6/2003 | Von Arx et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199790 A1 | 10/2003 | Boecker et al. |
| 2003/0212379 A1 | 11/2003 | Bylund et al. |
| 2003/0217966 A1 | 11/2003 | Tapsak et al. |
| 2003/0223906 A1 | 12/2003 | McAllister et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0034289 A1 | 2/2004 | Teller et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0063435 A1 | 4/2004 | Sakamoto et al. |
| 2004/0064068 A1 | 4/2004 | DeNuzzio et al. |
| 2004/0099529 A1 | 5/2004 | Mao et al. |
| 2004/0106858 A1 | 6/2004 | Say et al. |
| 2004/0116847 A1 | 6/2004 | Wall |
| 2004/0116866 A1 | 6/2004 | Gorman et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135684 A1 | 7/2004 | Steinthal et al. |
| 2004/0138588 A1 | 7/2004 | Saikley et al. |
| 2004/0147996 A1 | 7/2004 | Miazga et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0249254 A1 | 9/2004 | Racchini et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0219664 A1 | 11/2004 | Heller et al. |
| 2004/0223985 A1 | 11/2004 | Dunfiled et al. |
| 2004/0225338 A1 | 11/2004 | Lebel et al. |
| 2004/0236200 A1 | 11/2004 | Say et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004494 A1 | 1/2005 | Perez et al. |
| 2005/0010269 A1 | 1/2005 | Lebel et al. |
| 2005/0021066 A1 | 2/2005 | Kuhr et al. |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0043598 A1 | 2/2005 | Goode, Jr. et al. |
| 2005/0049179 A1 | 3/2005 | Davidson et al. |
| 2005/0070777 A1 | 3/2005 | Cho et al. |
| 2005/0090607 A1 | 4/2005 | Tapsak et al. |
| 2005/0096516 A1 | 5/2005 | Soykan et al. |
| 2005/0096520 A1 | 5/2005 | Maekawa et al. |
| 2005/0103624 A1 | 5/2005 | Bhullar et al. |
| 2005/0112169 A1 | 5/2005 | Brauker et al. |
| 2005/0113886 A1 | 5/2005 | Fischell et al. |
| 2005/0114068 A1 | 5/2005 | Chey et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0137530 A1 | 6/2005 | Campbell et al. |
| 2005/0143635 A1 | 6/2005 | Kamath et al. |
| 2005/0173245 A1 | 8/2005 | Feldman et al. |
| 2005/0176136 A1 | 8/2005 | Burd et al. |
| 2005/0182306 A1 | 8/2005 | Sloan |
| 2005/0187442 A1 | 8/2005 | Cho et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0211572 A1 | 9/2005 | Buck et al. |
| 2005/0214892 A1 | 9/2005 | Kovatchev et al. |
| 2005/0215871 A1 | 9/2005 | Feldman et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0251033 A1 | 11/2005 | Scarantino et al. |
| 2005/0272985 A1 | 12/2005 | Kotulla et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0009727 A1 | 1/2006 | O'Mahony et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0091006 A1 | 5/2006 | Wang et al. |
| 2006/0142651 A1 | 6/2006 | Brister et al. |
| 2006/0156796 A1 | 7/2006 | Burke et al. |
| 2006/0161664 A1 | 7/2006 | Motoyama |
| 2006/0166629 A1 | 7/2006 | Reggiardo |
| 2006/0169599 A1 | 8/2006 | Feldman et al. |
| 2006/0173406 A1* | 8/2006 | Hayes ............... A61B 5/14532 604/67 |
| 2006/0173444 A1 | 8/2006 | Choy et al. |
| 2006/0189863 A1 | 8/2006 | Peyser et al. |
| 2006/0193375 A1 | 8/2006 | Lee |
| 2006/0202805 A1 | 9/2006 | Schulman et al. |
| 2006/0211072 A1 | 9/2006 | Ryan et al. |
| 2006/0222566 A1 | 10/2006 | Brauker et al. |
| 2006/0224141 A1 | 10/2006 | Rush et al. |
| 2006/0226985 A1 | 10/2006 | Goodnow et al. |
| 2006/0229512 A1 | 10/2006 | Petisce et al. |
| 2006/0233839 A1 | 10/2006 | Jacquet |
| 2006/0247508 A1 | 11/2006 | Fennell |
| 2006/0253085 A1 | 11/2006 | Geismar et al. |
| 2006/0253086 A1 | 11/2006 | Moberg et al. |
| 2006/0253296 A1 | 11/2006 | Liisberg et al. |
| 2006/0258929 A1 | 11/2006 | Goode et al. |
| 2006/0281985 A1 | 12/2006 | Ward et al. |
| 2006/0287591 A1 | 12/2006 | Ocvirk et al. |
| 2006/0290496 A1 | 12/2006 | Peeters et al. |
| 2006/0293576 A1 | 12/2006 | Van Antwerp et al. |

(56) References Cited

U.S. PATENT DOCUMENTS

| | | |
|---|---|---|
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0027381 A1 | 2/2007 | Stafford |
| 2007/0032706 A1 | 2/2007 | Kamath et al. |
| 2007/0032717 A1 | 2/2007 | Brister et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0068807 A1 | 3/2007 | Feldman et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0093786 A1 | 4/2007 | Goldsmith et al. |
| 2007/0094216 A1 | 4/2007 | Mathias et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0118405 A1 | 5/2007 | Campbell et al. |
| 2007/0149875 A1 | 6/2007 | Ouyang et al. |
| 2007/0153705 A1 | 7/2007 | Rosar et al. |
| 2007/0156094 A1 | 7/2007 | Safabash et al. |
| 2007/0161880 A1 | 7/2007 | Say et al. |
| 2007/0163880 A1 | 7/2007 | Woo et al. |
| 2007/0173706 A1 | 7/2007 | Neinast et al. |
| 2007/0173710 A1 | 7/2007 | Petisce et al. |
| 2007/0191701 A1 | 8/2007 | Feldman et al. |
| 2007/0199818 A1 | 8/2007 | Petyt et al. |
| 2007/0203407 A1 | 8/2007 | Hoss et al. |
| 2007/0203966 A1 | 8/2007 | Brauker et al. |
| 2007/0208246 A1 | 9/2007 | Brauker et al. |
| 2007/0213657 A1 | 9/2007 | Jennewine et al. |
| 2007/0219496 A1 | 9/2007 | Kamen et al. |
| 2007/0227911 A1 | 10/2007 | Wang et al. |
| 2007/0228071 A1 | 10/2007 | Kamen et al. |
| 2007/0233013 A1 | 10/2007 | Schoenberg et al. |
| 2007/0235331 A1 | 10/2007 | Simpson et al. |
| 2007/0244379 A1 | 10/2007 | Boock et al. |
| 2007/0249922 A1 | 10/2007 | Peyser et al. |
| 2007/0255348 A1 | 11/2007 | Holtzclaw |
| 2007/0271285 A1 | 11/2007 | Eichorn et al. |
| 2007/0299617 A1 | 12/2007 | Willis |
| 2008/0004515 A1 | 1/2008 | Jennewine et al. |
| 2008/0009692 A1 | 1/2008 | Stafford |
| 2008/0017522 A1 | 1/2008 | Heller et al. |
| 2008/0021436 A1 | 1/2008 | Wolpert et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0200897 A1 | 2/2008 | Hoss et al. |
| 2008/0057484 A1 | 3/2008 | Miyata et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0060955 A1 | 3/2008 | Goodnow |
| 2008/0061961 A1 | 3/2008 | John |
| 2008/0066305 A1 | 3/2008 | Wang et al. |
| 2008/0071156 A1 | 3/2008 | Brister et al. |
| 2008/0077048 A1 | 3/2008 | Escutia et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0102441 A1 | 5/2008 | Chen et al. |
| 2008/0108942 A1 | 5/2008 | Brister et al. |
| 2008/0119703 A1 | 5/2008 | Brister et al. |
| 2008/0139910 A1 | 6/2008 | Mastrototaro et al. |
| 2008/0148873 A1 | 6/2008 | Wang |
| 2008/0156662 A1 | 7/2008 | Wu et al. |
| 2008/0161666 A1 | 7/2008 | Feldman et al. |
| 2008/0172205 A1 | 7/2008 | Breton et al. |
| 2008/0177149 A1 | 7/2008 | Weinert et al. |
| 2008/0182537 A1 | 7/2008 | Manku et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194934 A1 | 8/2008 | Ray et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208026 A1 | 8/2008 | Noujaim et al. |
| 2008/0314395 A1 | 8/2008 | Kovatchev et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234663 A1 | 9/2008 | Yodfat et al. |
| 2008/0242961 A1 | 10/2008 | Brister et al. |
| 2008/0242963 A1 | 10/2008 | Essenpreis et al. |
| 2008/0262469 A1 | 10/2008 | Brister et al. |
| 2008/0267823 A1 | 10/2008 | Wang et al. |
| 2008/0269723 A1 | 10/2008 | Mastrototaro et al. |
| 2008/0275313 A1 | 11/2008 | Brister et al. |
| 2008/0287761 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0300572 A1 | 12/2008 | Rankers et al. |
| 2008/0306353 A1* | 12/2008 | Douglas ............... G16H 40/63 600/301 |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312844 A1 | 12/2008 | Hayter et al. |
| 2008/0319279 A1 | 12/2008 | Ramsay et al. |
| 2008/0319295 A1 | 12/2008 | Bernstein et al. |
| 2009/0005665 A1 | 1/2009 | Hayter et al. |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0020502 A1 | 1/2009 | Bhullar et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054748 A1 | 2/2009 | Feldman et al. |
| 2009/0062633 A1 | 3/2009 | Brauker et al. |
| 2009/0062635 A1 | 3/2009 | Brauker et al. |
| 2009/0069750 A1 | 3/2009 | Schraga |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085873 A1 | 4/2009 | Betts et al. |
| 2009/0099436 A1 | 4/2009 | Brister et al. |
| 2009/0102678 A1 | 4/2009 | Mazza et al. |
| 2009/0105636 A1 | 4/2009 | Hayter et al. |

(56) References Cited

U.S. PATENT DOCUMENTS

| | | |
|---|---|---|
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163789 A1 | 6/2009 | Say et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0227855 A1 | 9/2009 | Hill et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0259118 A1 | 10/2009 | Feldman et al. |
| 2009/0275817 A1 | 11/2009 | Feldman et al. |
| 2009/0287073 A1 | 11/2009 | Boock et al. |
| 2009/0287074 A1 | 11/2009 | Shults et al. |
| 2009/0292188 A1 | 11/2009 | Hoss et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0056993 A1* | 3/2010 | Chase ............... A61M 5/14276 604/66 |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121169 A1 | 5/2010 | Petisce et al. |
| 2010/0141656 A1 | 6/2010 | Krieftewirth |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0191082 A1 | 7/2010 | Brister et al. |
| 2010/0234710 A1 | 9/2010 | Budiman et al. |
| 2010/0274111 A1 | 10/2010 | Say et al. |
| 2010/0280441 A1 | 11/2010 | Willinska et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0077490 A1 | 3/2011 | Simpson et al. |
| 2011/0097090 A1 | 4/2011 | Cao |
| 2011/0148905 A1 | 6/2011 | Simmons et al. |
| 2011/0208027 A1 | 8/2011 | Wagner et al. |
| 2011/0257895 A1 | 10/2011 | Brauker et al. |
| 2011/0263958 A1 | 10/2011 | Brauker et al. |
| 2011/0320130 A1 | 12/2011 | Valdes et al. |
| 2012/0078071 A1 | 3/2012 | Bohm et al. |
| 2012/0108934 A1 | 5/2012 | Valdes et al. |
| 2012/0173200 A1 | 7/2012 | Breton et al. |
| 2012/0190989 A1 | 7/2012 | Kaiser et al. |
| 2012/0226121 A1 | 9/2012 | Kamath et al. |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| WO | WO-1996/025089 | 8/1996 |
| WO | WO-1996/035370 | 11/1996 |
| WO | WO-2000/049940 | 8/2000 |
| WO | WO-2000/059370 | 10/2000 |
| WO | WO-2001/052935 | 7/2001 |
| WO | WO-2001/054753 | 8/2001 |
| WO | WO-2002/016905 | 2/2002 |
| WO | WO-2003/076893 | 9/2003 |
| WO | WO-2003/082091 | 10/2003 |
| WO | WO-2006/024671 | 3/2006 |
| WO | WO-2008099288 A2 * | 8/2008 ........... A61B 5/0533 |

OTHER PUBLICATIONS

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Bremer, T. M., et al., "Benchmark Data from the Literature for Evaluation of New Glucose Sensing Technologies", *Diabetes Technology & Therapeutics*, vol. 3, No. 3, 2001, pp. 409-418.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

(56) References Cited

OTHER PUBLICATIONS

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Jobst, G., et al., "Thin-Film Microbiosensors for Glucose-Lactate Monitoring", *Analytical Chemistry*, vol. 68, No. 18, 1996, pp. 3173-3179.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Kuure-Kinsey, M., et al., "A Dual-Rate Kalman Filter for Continuous Glucose Monitoring", *Proceedings of the 28th IEEE, EMBS Annual International Conference*, New York City, 2006, pp. 63-66.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Lortz, J., et al., "What is Bluetooth? We Explain The Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Mougiakakou, et al., "A Real Time Simulation Model of Glucose-Insulin Metabolism for Type 1 Diabetes Patients", *Proceedings of the 2005 IEEE*, 2005, pp. 298-301.

Panteleon, A. E., et al., "The Role of the Independent Variable to Glucose Sensor Calibration", *Diabetes Technology & Therapeutics*, vol. 5, No. 3, 2003, pp. 401-410.

Parker, R., et al., "Robust H∞ Glucose Control in Diabetes Using a Physiological Model", *AIChE Journal*, vol. 46, No. 12, 2000, pp. 2537-2549.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

(56) References Cited

OTHER PUBLICATIONS

Wilson, G. S., et al., "Progress Toward the Development of an Implantable Sensor for Glucose", *Clinical Chemistry*, vol. 38, No. 9, 1992, pp. 1613-1617.
PCT Application No. PCT/US2009/050602, International Preliminary Report on Patentability dated Jan. 27, 2011.
PCT Application No. PCT/US2009/050602, International Search Report and Written Opinion of the International Searching Authority dated Sep. 10, 2009.
U.S. Appl. No. 12/503,022, Advisory Action dated Feb. 20, 2013.
U.S. Appl. No. 12/503,022, Notice of Allowance dated Aug. 22, 2014.
U.S. Appl. No. 12/503,022, Office Action dated Dec. 13, 2011.
U.S. Appl. No. 12/503,022, Office Action dated Oct. 5, 2012.

* cited by examiner

CLOSED LOOP CONTROL SYSTEM INTERFACE AND METHODS

RELATED APPLICATIONS

The present application is a continuation of U.S. patent application Ser. No. 14/529,026 filed Oct. 30, 2014, now U.S. Pat. No. 10,328,201, which is a continuation of U.S. patent application Ser. No. 12/503,022 filed Jul. 14, 2009, now U.S. Pat. No. 8,876,755, which claims priority under § 35 U.S.C. 119(e) to U.S. provisional application No. 61/080,677 filed Jul. 14, 2008 entitled "Closed Loop Control System Interface and Methods", the disclosures of each of which are incorporated herein by reference for all purposes.

BACKGROUND

Commercial devices and systems for monitoring glucose levels in a patient are currently available. For example, FreeStyle Navigator® Continuous Glucose Monitoring System available from Abbott Diabetes Care Inc., provides diabetes management tools for monitoring glucose levels of a patient over an extended time period using a subcutaneous analyte sensor, for example, in contact with interstitial fluid of the patient. Such devices and systems provide real time glucose information to the patient to assist in improving glycemic control. Also available are infusion devices such as external insulin pumps which are programmable to deliver insulin based on a programmed delivery profile to diabetic patients, for example. Typically, such pumps are programmed to deliver a predetermined basal delivery profile, and periodically administer user specified bolus dosage or temporary basal delivery.

In recent years, developments have been on going in closed loop therapy systems which automate the control of the insulin delivery based on real time feedback of the patient's glucose levels. There are known closed loop control algorithms that are intended to model artificial pancreas to provide a fully automated and integrated system of glucose monitoring and insulin delivery.

With the development of different algorithms for closed loop control as well as glucose monitoring systems and infusion devices, integration of such components to provide compatibility has become a challenge.

SUMMARY

In view of the foregoing, a closed loop system interface device and methods are provided in accordance with various embodiments of the present disclosure which provide compatibility with any developing closed loop algorithm, and integration with the analyte monitoring system.

In one aspect, method and apparatus for calling a programmed function in conjunction with execution of one or more commands related to a closed loop control algorithm, receiving one or more data in response to the one or more commands over a data interface, and executing the one or more commands related to the closed loop control algorithm based on the received one or more data are provided.

These and other objects, features and advantages of the present disclosure will become more fully apparent from the following detailed description of the embodiments, the appended claims and the accompanying drawings.

DETAILED DESCRIPTION

Figure 1:
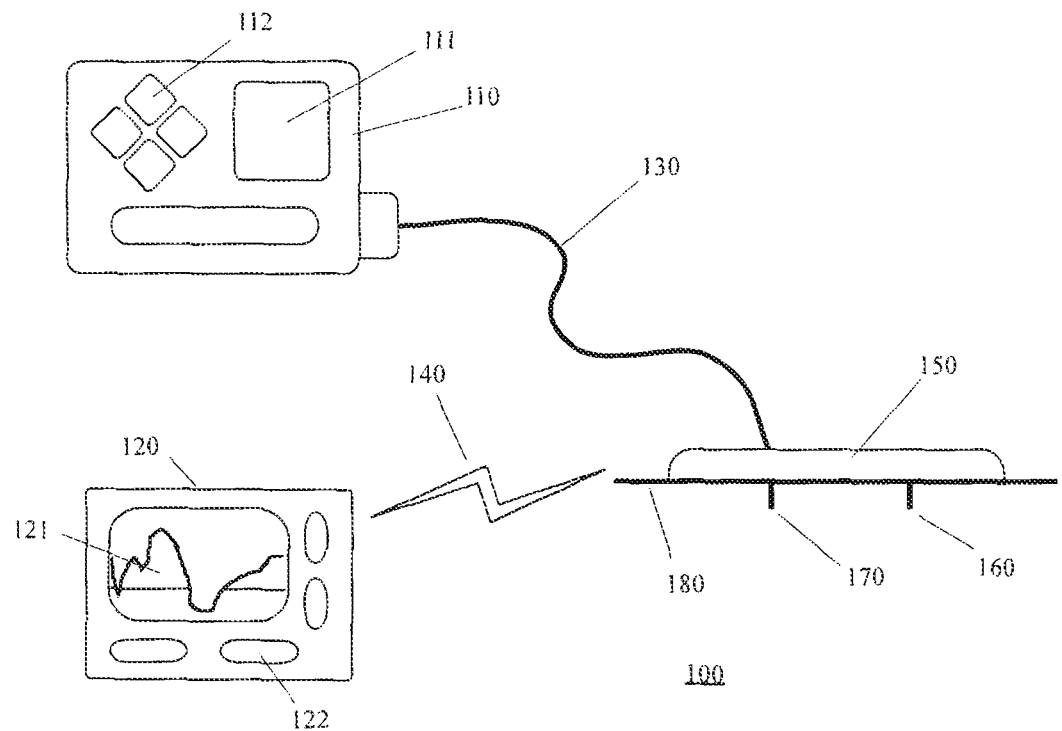
FIG. 1 illustrates an integrated infusion device and analyte monitoring system in accordance with one embodiment of the present disclosure.

FIG. 1 illustrates an integrated infusion device and analyte monitoring system in accordance with one embodiment of the present disclosure. Referring to FIG. 1, the integrated infusion device and analyte monitoring system 100 in one embodiment of the present disclosure includes an infusion device 110 connected to an infusion tubing 130 for liquid transport or infusion, and which is further coupled to a cannula 170. As can be seen from FIG. 1, the cannula 170 is configured to be mountably coupled to a transmitter unit 150, where the transmitter unit 150 is also mountably coupled to an analyte sensor 160. Also provided is an analyte monitor unit 120 which is configured to wirelessly communicate with the transmitter unit 150 over a communication path 140.

Referring to FIG. 1, in one embodiment of the present disclosure, the transmitter unit 150 is configured for unidirectional wireless communication over the communication path 140 to the analyte monitor unit 120. In one embodiment, the analyte monitor unit 120 may be configured to include a transceiver unit (not shown) for bidirectional communication over the communication path 140. The transmitter unit 150 in one embodiment may be configured to periodically and/or intermittently transmit signals associated with analyte levels detected by the analyte sensor 160 to the analyte monitor unit 120. The analyte monitor unit 120 may be configured to receive the signals from the transmitter unit 150 and in one embodiment, is configured to perform data storage and processing based on one or more preprogrammed or predetermined processes.

For example, in one embodiment, the analyte monitor unit 120 is configured to store the received signals associated with analyte levels in a data storage unit (not shown). Alternatively, or in addition, the analyte monitor unit 120 may be configured to process the signals associated with the analyte levels to generate trend indication by, for example, visual display of a line chart or an angular icon based display for output display on its display unit 121. Additional information may be output displayed on the display unit 121 of the analyte monitor unit 120 including, but not limited to, the substantially contemporaneous and real time analyte level of the patient received from the transmitter unit 150 as detected by the sensor 160. The real time analyte level may be displayed in a numeric format or in any other suitable format which provides the patient with the accurate measurement of the substantially real time analyte level detected by the sensor 160.

Additional analytes that may be monitored or determined by the sensor 160 include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Referring back to FIG. 1, the sensor 160 may include a short term (for example, 3 day, 5 day or 7 day use) analyte sensor which is replaced after its intended useful life. Moreover, in one embodiment, the sensor 160 is configured to be positioned subcutaneous to the skin of the patient such that at least a portion of the analyte sensor is maintained in fluid contact with the patient's analyte such as, for example, interstitial fluid or blood. In addition, the cannula 170, which is configured to similarly be positioned under the patient's skin, is connected to the infusion tubing 130 of the infusion device 110 so as to deliver medication such as insulin to the patient. Moreover, in one embodiment, the cannula 170 is configured to be replaced with the replacement of the sensor 160.

In one aspect of the present disclosure, the cannula 170 and the sensor 160 may be configured to be subcutaneously positioned under the skin of the patient using an insertion mechanism (not shown) such as an insertion gun which may include, for example, a spring biased or loaded insertion mechanism to substantially accurately position the cannula 170 and the sensor 160 under the patient's skin. In this manner, the cannula 170 and the sensor 160 may be subcutaneously positioned with substantially little or no perceived pain by the patient. Alternatively, the cannula 170 and/or the sensor 160 may be configured to be manually inserted by the patient through the patient's skin. After positioning the cannula 170 and the sensor 160, they may be substantially firmly retained in position by an adhesive layer 180 which is configured to adhere to the skin of the patient for the duration of the time period during which the sensor 160 and the cannula 170 are subcutaneously positioned.

Moreover, in one embodiment, the transmitter unit 150 may be mounted after the subcutaneous positioning of the sensor 160 and the cannula 150 so as to be in electrical contact with the sensor electrodes. Similarly, the infusion tubing 130 may be configured to operatively couple to the housing of the transmitter unit 150 so as to be in accurately positioned for alignment with the cannula 170 and to provide a substantially water tight seal. Additional detailed description of the analyte monitoring system including the sensor 160, transmitter unit 150 and the analyte monitor unit 120 is provided in U.S. Pat. No. 6,175,752, assigned to the assignee of the present disclosure, Abbott Diabetes Care Inc., the disclosure of which is incorporated by reference for all purposes.

Referring back to FIG. 1, the infusion device 110 may include capabilities to program basal profiles, calculation of bolus doses including, but is not limited to, correction bolus, carbohydrate bolus, extended bolus, and dual bolus, which may be performed by the patient using the infusion device 110, and may be based on one or more factors including the patient's insulin sensitivity, insulin on board, intended carbohydrate intake (for example, for the carbohydrate bolus calculation prior to a meal), the patient's measured or detected glucose level, and the patient's glucose trend information. In a further embodiment, the bolus calculation capabilities may also be provided in the analyte monitor unit 120.

In one embodiment, the analyte monitor unit 120 is configured with a substantially compact housing that can be easily carried by the patient. In addition, the infusion device 110 similarly may be configured as a substantially compact device which can be easily and conveniently worn on the patient's clothing (for example, housed in a holster or a carrying device worn or clipped to the patient's belt or other parts of the clothing). Referring yet again to FIG. 1, the analyte monitor unit 120 and/or the infusion device 110 may include a user interface such as information input mechanism 112, 122 by the patient as well as data output including, for example, the display unit 121 on the analyte monitor unit 120, or similarly a display unit 111 on the infusion device 110.

One or more audio output devices such as, for example, speakers or buzzers may be integrated with the housing of the infusion device 110 and/or the analyte monitor unit 120 so as to output audible alerts or alarms based on the occurrence of one or more predetermined conditions associated with the infusion device 110 or the analyte monitor unit 120. For example, the infusion device 110 may be configured to output an audible alarm or alert to the patient upon detection of an occlusion in the infusion tubing 130 or the occurrence of a timed event such as a reminder to prime the infusion tubing upon replacement of the cannula 170, and the like. The analyte monitor unit 120 may similarly be configured to output an audible alarm or alert when a predetermined condition or a pre-programmed event occurs, such as, for example, a reminder to replace the sensor 160 after its useful life (of 3 days, 5 days or 7 days), or one or more alerts associated with the data received from the transmitter unit 150 corresponding to the patient's monitored analyte levels. Such alerts or alarms may include a warning alert to the patient that the detected analyte level is beyond a predetermined threshold level, or the trend of the detected analyte levels within a given time period is indicative of a significant condition such as potential hyperglycemia or hypoglycemia, which require attention or corrective action. It is to be noted that the examples of audible alarms and/or alerts are described above for illustrative purposes only, that within the scope of the present disclosure, other events or conditions may be programmed into the infusion device 110 or the analyte monitor unit 120 or both, so as to alert or notify the patient of the occurrence or the potential occurrence of such events or conditions.

In addition, within the scope of the present disclosure, audible alarms may be output alone, or in combination with one or more of a visual alert such as an output display on the display unit 111, 121 of the infusion device 110 or the analyte monitor unit 120, respectively, or vibratory alert which would provide a tactile indication to the patient of the associated alarm and/or alert.

Moreover, referring yet again to FIG. 1, while one analyte monitor unit 120 and one transmitter unit 150 are shown, within the scope of the present disclosure, additional analyte monitor units or transmitter units may be provided such that, for example, the transmitter unit 150 may be configured to transmit to multiple analyte monitor units substantially simultaneously. Alternatively, multiple transmitter units coupled to multiple sensors concurrently in fluid contact with the patient's analyte may be configured to transmit to the analyte monitor unit 120, or to multiple analyte monitor units. For example, an additional transmitter unit coupled to an additional sensor may be provided in the integrated infusion device and analyte monitoring system 100 which does not include the cannula 170, and which may be used to perform functions associated with the sensor 160 such as sensor calibration, sensor data verification, and the like.

In one embodiment, the transmitter unit 150 is configured to transmit the sampled data signals received from the sensor 160 without acknowledgement from the analyte monitor unit 120 that the transmitted sampled data signals have been received. For example, the transmitter unit 150 may be configured to transmit the encoded sampled data signals at a fixed rate (e.g., at one minute intervals) after the completion of the initial power on procedure. Likewise, the analyte monitor unit 120 may be configured to detect such transmitted encoded sampled data signals at predetermined time intervals. Alternatively, the transmitter unit 150 and the analyte monitor unit 120 may be configured for bi-directional communication over the communication path 140.

Additionally, in one aspect, the analyte monitor unit 120 may include two sections. The first section of the analyte monitor unit 120 may include an analog interface section that is configured to communicate with the transmitter unit 150 via the communication path 140. In one embodiment, the analog interface section may include an RF receiver and an antenna for receiving and amplifying the data signals from the transmitter unit 150, which are thereafter, demodulated with a local oscillator and filtered through a band-pass filter. The second section of the analyte monitor unit 120 may include a data processing section which is configured to process the data signals received from the transmitter unit 150 such as by performing data decoding, error detection and correction, data clock generation, and data bit recovery, for example.

In operation, upon completing the power-on procedure, the analyte monitor unit 120 is configured to detect the presence of the transmitter unit 150 within its range based on, for example, the strength of the detected data signals received from the transmitter unit 150 or a predetermined transmitter identification information. Upon successful synchronization with the transmitter unit 150, the analyte monitor unit 120 is configured to begin receiving from the transmitter unit 150 data signals corresponding to the patient's detected analyte, for example glucose, levels.

Referring again to FIG. 1, the analyte monitor unit 120 or the infusion device 110, or both may be configured to further communicate with a data processing terminal (not shown) which may include a desktop computer terminal, a data communication enabled kiosk, a laptop computer, a handheld computing device such as a personal digital assistant (PDAs), or a data communication enabled mobile telephone, and the like, each of which may be configured for data communication via a wired or a wireless connection. The data processing terminal for example may include physician's terminal and/or a bedside terminal in a hospital environment, for example.

The communication path 140 for data communication between the transmitter unit 150 and the analyte monitor unit 120 of FIG. 1 may include an RF communication link, Bluetooth® communication link, infrared communication link, or any other type of suitable wireless communication connection between two or more electronic devices. The data communication link may also include a wired cable connection such as, for example, but not limited to, an RS232 connection, USB connection, or serial cable connection.

Referring yet again to FIG. 1, in a further aspect of the present disclosure, the analyte monitor unit 120 or the infusion device 110 (or both) may also include a test strip port configured to receive a blood glucose test strip for discrete sampling of the patient's blood for glucose level determination. An example of the functionality of blood glucose test strip meter unit may be found in Freestyle® Blood Glucose Meter available from the assignee of the present disclosure, Abbott Diabetes Care Inc.

In the manner described above, in one embodiment of the present disclosure, the cannula 170 for infusing insulin or other suitable medication is integrated with the adhesive patch 180 for the sensor 160 and the transmitter unit 150 of the analyte monitoring system. Accordingly, only one on-skin patch can be worn by the patient (for example, on the skin of the abdomen) rather than two separate patches for the infusion device cannula 170, and the analyte monitoring system sensor 160 (with the transmitter unit 150). Thus, the Type-1 diabetic patient may conveniently implement infusion therapy in conjunction with real time glucose monitoring while minimizing potential skin irritation on the adhesive patch 180 site on the patient's skin, and thus provide more insertion sites with less irritation.

In addition, the integrated infusion device and analyte monitoring system 100 as shown in FIG. 1 may be configured such that the infusion tubing 130 may be disconnected from the infusion device 110 as well as from the housing of the transmitter unit 150 (or the adhesive patch 180) such that, optionally, the patient may configure the system as continuous analyte monitoring system while disabling the infusion device 110 functionality.

Moreover, in accordance with one embodiment of the present disclosure, the patient may better manage the physiological conditions associated with diabetes by having substantially continuous real time glucose data, trend information based on the substantially continuous real time glucose data, and accordingly, modify or adjust the infusion levels delivered by the infusion device 110 from the pre-programmed basal profiles that the infusion device 110 is configured to implement.

Figure 2:
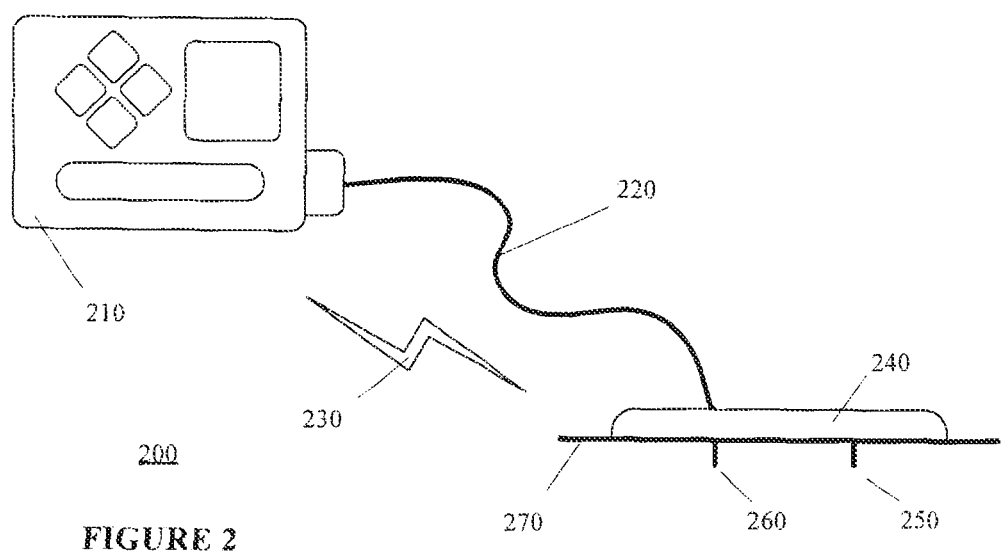
FIG. 2 illustrates an integrated infusion device and analyte monitoring system in accordance with another embodiment of the present disclosure.

FIG. 2 illustrates an integrated infusion device and analyte monitoring system in accordance with another embodiment of the present disclosure. Referring to FIG. 2, the integrated infusion device and analyte monitoring system 200 in one embodiment of the present disclosure includes an integrated infusion device and analyte monitor unit 210 which is coupled to an infusion tubing 220 connected to the cannula 260. Also shown in FIG. 2 is a transmitter unit 240 which is in electrical contact with an analyte sensor 250, where the cannula 260 and the analyte sensor 250 are subcutaneously positioned under the skin of the patient, and retained in position by an adhesive layer or patch 270.

Referring to FIG. 2, the integrated infusion device and analyte monitor unit 210 is configured to wirelessly communicate with the transmitter unit 240 over a communication path 230 such as an RF communication link. Compared with the embodiment shown in FIG. 1, it can be seen that in the embodiment shown in FIG. 2, the infusion device and the analyte monitor are integrated into a single housing 210. In this manner, the transmitter unit 240 may be configured to transmit signals corresponding to the detected analyte levels received from the analyte sensor 250 to the integrated infusion device and analyte monitor unit 210 for data analysis and processing.

Accordingly, the patient may conveniently receive real time glucose levels from the transmitter unit 240 and accordingly, determine whether to modify the existing basal profile (s) in accordance with which insulin is delivered to the patient. In this manner, the functionalities of the analyte monitor unit may be integrated within the compact housing of the infusion device to provide additional convenience to the patient by, for example, providing the real time glucose data as well as other relevant information such as glucose trend data to the user interface of the infusion device, so that the patient may readily and easily determine any suitable modification to the infusion rate of the insulin pump.

In one embodiment, the configurations of each component shown in FIG. 2 including the cannula 260, the analyte sensor 250, the transmitter unit 240, the adhesive layer 270, the communication path 230, as well as the infusion tubing 220 and the functionalities of the infusion device and the analyte monitor are substantially similar to the corresponding respective component as described above in conjunction with FIG. 1.

Accordingly, in one embodiment of the present disclosure, the additional convenience may be provided to the patient in maintaining and enhancing diabetes management by, for example, having a single integrated device such as the integrated infusion device and analyte monitor unit 210 which would allow the patient to easily manipulate and manage insulin therapy using a single user interface system of the integrated infusion device and analyte monitor unit 210. Indeed, by providing many of the information associated with the glucose levels and insulin infusion information in one device, the patient may be provided with the additional convenience in managing diabetes and improving insulin therapy.

Figure 3:
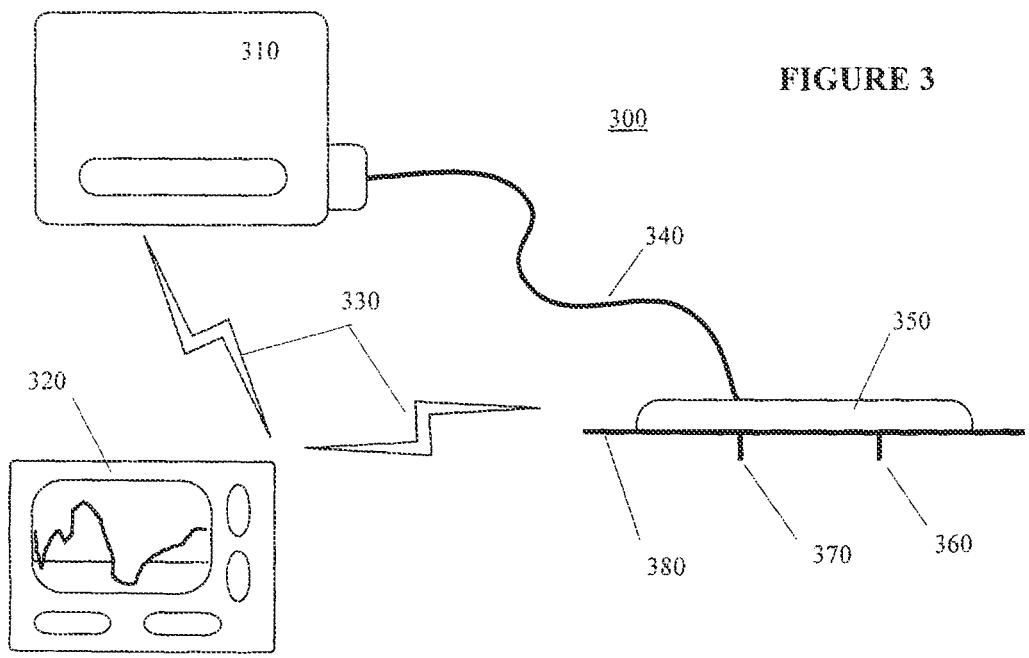
FIG. 3 illustrates an integrated infusion device and analyte monitoring system in accordance with yet another embodiment of the present disclosure.

FIG. 3 illustrates an integrated infusion device and analyte monitoring system in accordance with yet another embodiment of the present disclosure. Referring to FIG. 3, the integrated infusion device and analyte monitoring system 300 in one embodiment of the present disclosure includes an infusion device 310 connected to an infusion tubing 340 coupled to a cannula 370. The cannula 370 is configured to be positioned subcutaneously under the patient's skin and substantially retained in position by an adhesive layer 380. Also retained in position, as discussed above and similar to the embodiments described in conjunction with FIGS. 1-2, is an analyte sensor 360 also positioned subcutaneously under the patient's skin and maintained in fluid contact with the patient's analyte. A transmitter unit 350 is provided so as to be electrically coupled to the analyte sensor 360 electrodes. Also, as can be seen from FIG. 3, in one embodiment, the infusion tubing 340 is connected to the housing of the transmitter unit 350 so as to connect to the cannula 370 disposed under the patient's skin.

Referring to FIG. 3, also provided is an analyte monitoring unit 320 configured to wirelessly communicate with the transmitter unit 350 to receive data therefrom associated with the analyte levels of the patient detected by the analyte sensor 360. Referring to FIG. 3, in one embodiment, the infusion device 310 does not include a user interface such as a display unit and/or an input unit such as buttons or a jog dial. Instead, the user interface and control mechanism is provided on the analyte monitoring unit 320 such that the analyte monitoring unit 320 is configured to wirelessly control the operation of the infusion device 310 and further, to suitably program the infusion device 310 to execute pre-programmed basal profile(s), and to otherwise control the functionality of the infusion device 310.

More specifically, all of the programming and control mechanism for the infusion device 310 is provided in the analyte monitoring unit 320 such that when the patient is wearing the infusion device 310, it may be worn discreetly under clothing near the infusion site on the patient's skin (such as abdomen), while still providing convenient access to the patient for controlling the infusion device 310 through the analyte monitoring unit 320.

In addition, in one embodiment, the configurations of each component shown in FIG. 3 including the cannula 370, the analyte sensor 360, the transmitter unit 350, the adhesive layer 380, the communication path 330, as well as the infusion tubing 340 and the functionalities of the infusion device and the analyte monitoring unit 320 are substantially similar to the corresponding respective component as described above in conjunction with FIG. 1. However, the infusion device 310 in the embodiment shown in FIG. 3 is configured with a transceiver or an equivalent communication mechanism to communicate with the analyte monitoring unit 320.

In this manner, in one embodiment of the present disclosure, configuration of the infusion device 310 without a user interface provides a smaller and lighter housing and configuration for the infusion device 310 which would enhance the comfort in wearing and/or carrying the infusion device 310 with the patient. Moreover, since the control and programming functions of the infusion device 310 is provided on the analyte monitoring unit 320, the patient may conveniently program and/or control the functions and operations of the infusion device 310 without being tethered to the infusion tubing 340 attached to the cannula 370 which is positioned under the patient's skin. In addition, since the programming and control of the infusion device 310 is remotely performed on the analyte monitoring unit 320, the infusion tubing 340 may be shorter and thus less cumbersome.

Figure 4:
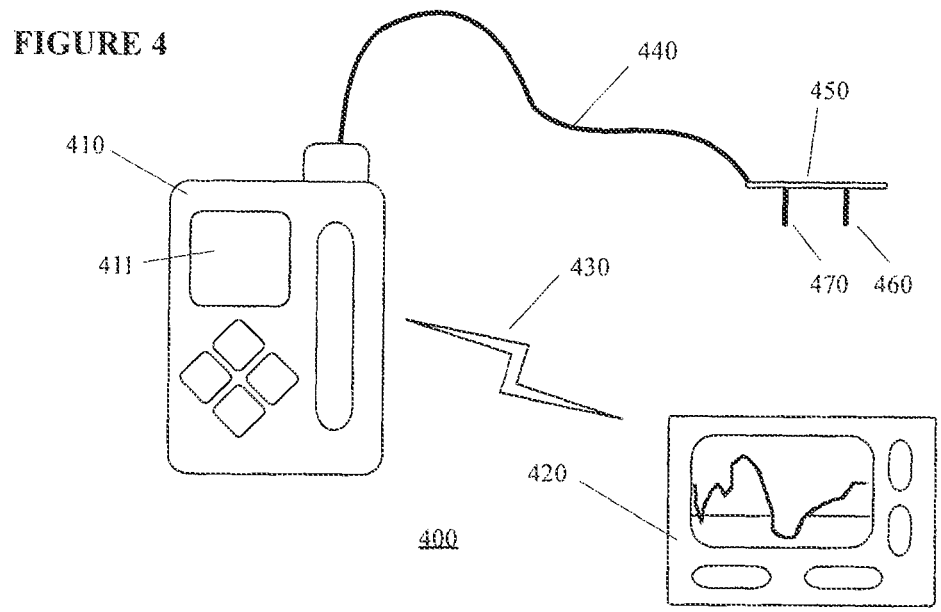
FIG. 4 illustrates an integrated infusion device and analyte monitoring system in accordance with still another embodiment of the present disclosure.

FIG. 4 illustrates an integrated infusion device and analyte monitoring system in accordance with still another embodiment of the present disclosure. Referring to FIG. 4, the integrated infusion device and analyte monitoring system 400 in one embodiment of the present disclosure includes an infusion device 410 configured to wirelessly communicate with an analyte monitoring unit 420 over a communication path 430 such as an RF (radio frequency) link. In addition, as can be further seen from FIG. 4, the infusion device 410 is connected to an infusion tubing 440 which has provided therein integral wires connected to the analyte sensor electrodes. As discussed in further detail below, the measured analyte levels of the patient is received by the infusion device 410 via the infusion tubing 440 and transmitted to the analyte monitoring unit 420 for further processing and analysis.

More specifically, referring to FIG. 4, the integrated infusion device and analyte monitoring system 400 includes a patch 450 provided with a cannula 470 and an analyte sensor 460. The cannula 470 is configured to deliver or infuse medication such as insulin from the infusion device 410 to the patient. That is, in one embodiment, the cannula 470 and the analyte sensor 460 are configured to be positioned subcutaneous to the patient's skin. The analyte sensor 460 is configured to be positioned in fluid contact with the patient's analyte.

In this manner, the analyte sensor 460 is electrically coupled to integral wires provided within the infusion tubing 440 so as to provide signals corresponding to the measured or detected analyte levels of the patient to the infusion device 410. In one embodiment, the infusion device 410 is configured to perform data analysis and storage, such that the infusion device 410 may be configured to display the real time measured glucose levels to the patient on display unit 411. In addition to or alternatively, the infusion device 410 is configured to wirelessly transmit the received signals from the analyte sensor 460 to the analyte monitoring unit 420 for data analysis, display, and/or storage and the analyte monitoring unit 420 may be configured to remotely control the functions and features of the infusion device 410 providing additional user convenience and discreteness.

Referring back to FIG. 4, in one embodiment, the patch 450 may be configured to be substantially small without a transmitter unit mounted thereon, and provided with a relatively small surface area to be attached to the patient's skin. In this manner, the patient may be provided with added comfort in having a substantially compact housing mounted on the skin (attached with an adhesive layer, for example), to infuse medication such as insulin, and for continuous analyte monitoring with the analyte sensor 460.

Figure 5:
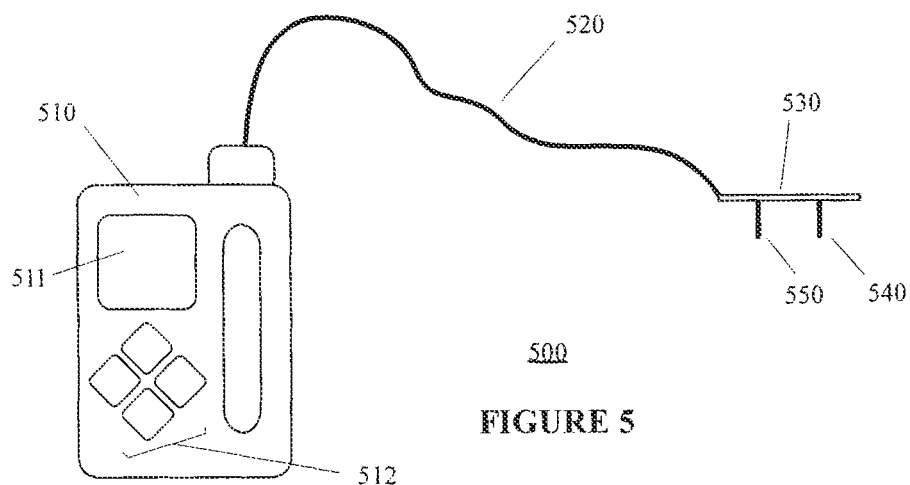
FIG. 5 illustrates an integrated infusion device and analyte monitoring system in accordance with still a further embodiment of the present disclosure.

FIG. 5 illustrates an integrated infusion device and analyte monitoring system in accordance with still a further embodiment of the present disclosure. As compared with the embodiment shown in FIG. 4, the integrated infusion device and analyte monitoring system 500 of FIG. 5 includes an integrated infusion device and analyte monitoring unit 510. Accordingly, one user interface is provided to the user including the display unit 511 and input buttons 512 provided on the housing of the integrated infusion device and analyte monitoring unit 510. Also shown in FIG. 5 are infusion tubing 520 with integral wires disposed therein and connected to an analyte sensor 540 with electrodes in fluid contact with the patient's analyte. Moreover, as can be seen from FIG. 5, an adhesive patch 530 is provided to retain the subcutaneous position of a cannula 550 and the analyte sensor 540 in the desired positions under the patient's skin.

Optionally, the integrated infusion device and analyte monitoring unit 510 may be provided with wireless or wired communication capability so to communicate with a remote terminal such as a physician's computer terminal over a wireless communication path such as RF communication link, or over a cable connection such as a USB connection, for example. Referring back to FIG. 5, in one embodiment of the present disclosure, the diabetic patient using an infusion therapy is provided with less components to handle or manipulate further simplifying insulin therapy and glucose level monitoring and management.

Figure 6:
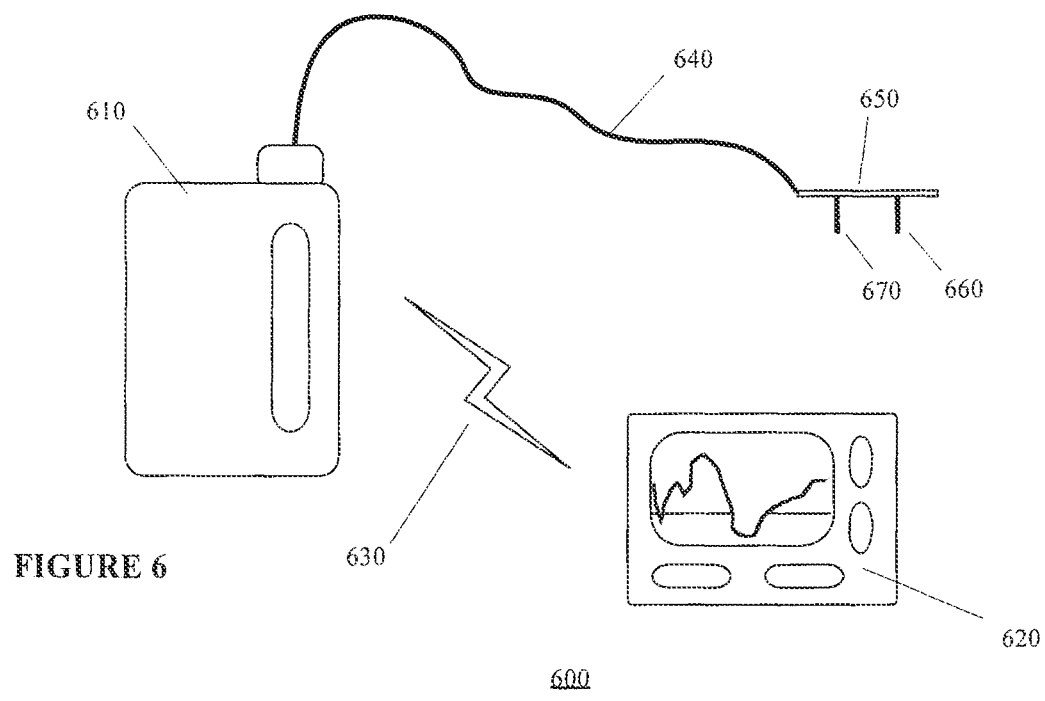
FIG. 6 illustrates an integrated infusion device and monitoring system in accordance with yet still a further embodiment of the present disclosure.

FIG. 6 illustrates an integrated infusion device and monitoring system in accordance with yet still a further embodiment of the present disclosure. Referring to FIG. 6, the integrated infusion device and analyte monitoring system 600 is provided with an infusion device without a user interface, and configured to wirelessly communicate with an analyte monitoring unit 620 over a communication path 630 such as an RF link. The infusion device 610 which may be provided in a compact housing since it does not incorporate the components associated with a user interface, is connected to an infusion tubing 640 having disposed therein integral wires correspondingly connected to the electrodes of analyte sensor 660 in fluid contact with the patient's analyte. In addition, the compact adhesive patch 650 in one embodiment is configured to retain cannula 670 and the analyte sensor 660 in the desired position under the skin of the patient.

Similar to the embodiment shown in FIG. 3, the analyte monitoring unit 620 is configured to control and program the infusion device 610 over the communication link 630. In this manner, the control and programming functions of the infusion device 610 may be remotely performed by the analyte monitoring unit 620, providing convenience to the patient.

Figure 7A:
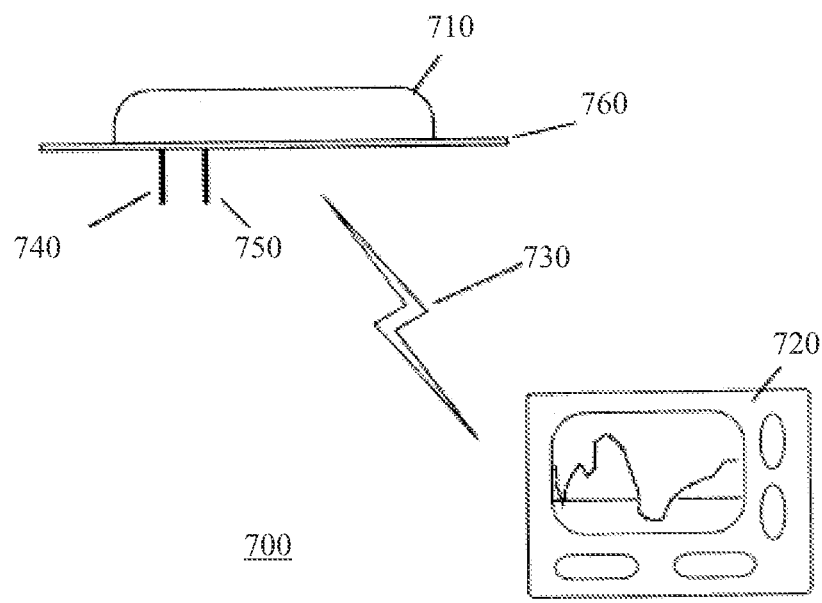
FIG. 7A illustrates an integrated infusion device and analyte monitoring system with the infusion device and the monitoring system transmitter integrated into a single patch worn by the patient in accordance with one embodiment of the present disclosure and FIG. 7B illustrates a top view of the patch of FIG. 7A.
Figure 7B:
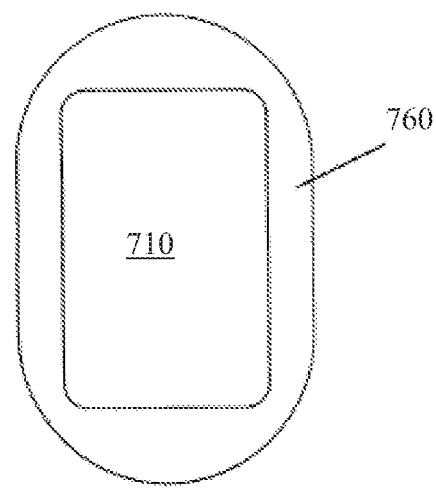

FIG. 7A illustrates an integrated infusion device and analyte monitoring system with the infusion device and the monitoring system transmitter integrated into a single patch worn by the patient in accordance with one embodiment of the present disclosure and FIG. 7B illustrates a top view of the patch of FIG. 7A. Referring to FIGS. 7A and 7B, the integrated infusion device and analyte monitoring system 700 includes an integrated patch pump and transmitter unit 710 provided on an adhesive layer 760, and which is configured to be placed on the skin of the patient, so as to securely position cannula 750 and analyte sensor 740 subcutaneously under the skin of the patient. The housing of the integrated infusion pump and transmitter unit 710 is configured in one embodiment to include the infusion mechanism to deliver medication such as insulin to the patient via the cannula 750.

In addition, the integrated patch pump and transmitter unit 710 is configured to transmit signals associated with the detected analyte levels measured by the analyte sensor 740, over a wireless communication path 730 such as an RF link. The signals are transmitted from the on body integrated patch pump and transmitter unit 710 to a controller unit 720 which is configured to control the operation of the integrated patch pump and transmitter unit 710, as well as to receive the transmitted signals from the integrated patch pump and transmitter unit 710 which correspond to the detected analyte levels of the patient.

Referring back to FIGS. 7A and 7B, in one embodiment, the infusion mechanism of the integrated patch pump and transmitter unit 710 may include the infusion device of the type described in U.S. Pat. No. 6,916,159 assigned to the assignee of the present disclosure, Abbott Diabetes Care Inc., the disclosure of which is incorporated by reference for all purposes. In addition, while a wireless communication over the communication path 730 is shown in FIG. 7A, the wireless communication path 730 may be replaced by a set of wires to provide a wired connection to the controller unit 720.

In this manner, in one embodiment of the present disclosure, the integrated infusion device and analyte monitoring system 700 does not use an infusion tubing which may provide additional comfort and convenience to the patient by providing additional freedom from having to wear a cumbersome tubing.

Figure 8:
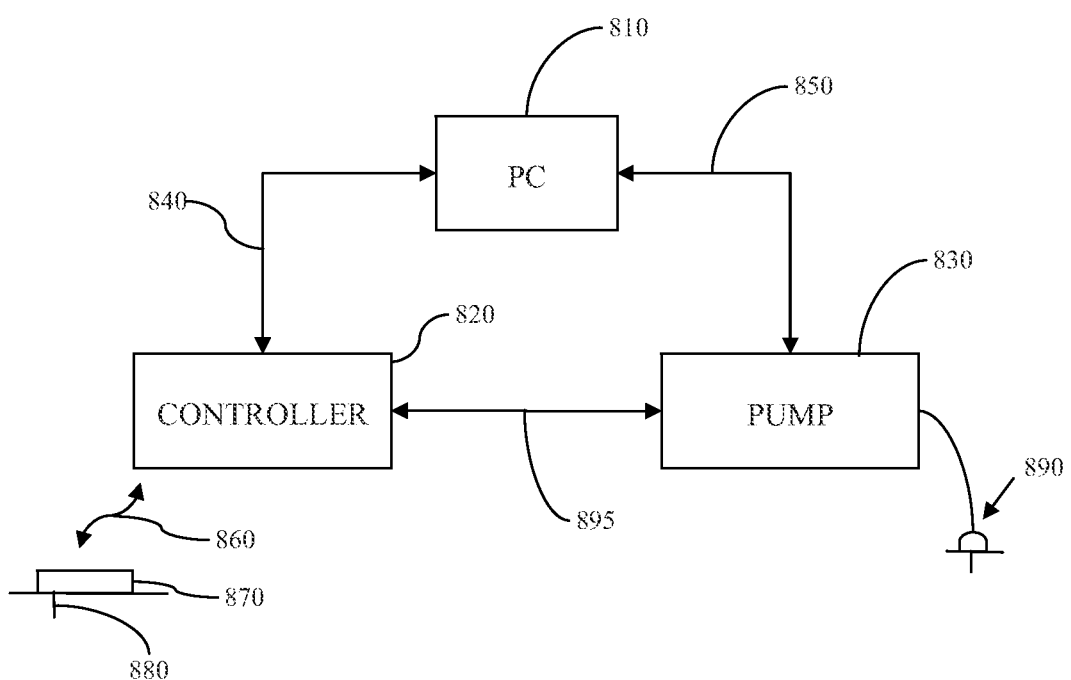
FIG. 8 illustrates a closed loop system interface for practicing one or more embodiments of the present disclosure.

FIG. 8 illustrates a closed loop system interface for practicing one or more embodiments of the present disclosure. Referring to the Figure, in one aspect, the closed loop architecture includes a PC terminal 810, such as a computer terminal which includes the predefined closed loop algorithm, in communication with a controller 820 and a pump 830. The controller 820 in one aspect is configured to receive analyte data over a data connection 860 such as an RF link, from a data transmitter 870 which is connected to an analyte sensor 880. In one aspect, the controller 820 in combination with the transmitter 870 and the analyte sensor 880 comprise the analyte monitoring system described above.

Referring again to FIG. 8, the pump 830 is connected to an infusion set/tubing 890 for delivering medication such as insulin to a user. While not shown, the analyte sensor 880 and the cannula of the infusion set/tubing is transcutaneously positioned under the skin layer of the patient to monitor analyte levels and deliver medication, respectively. As can be seen, there are provided data interface 840, 850 between the controller 820 and PC terminal 810, and the pump 830 and the PC terminal 810. In one aspect, the data interfaces 840, 850 include USB data connection for data transfer between the various components described. In a further aspect, the closed loop algorithm may be provided in the controller 820 in which case, the PC terminal 810 shown in FIG. 8 may be an optional device, and the data interface 840, 850 may be similarly optional. In such configuration, the controller 820 in one aspect may be configured to communicate with the pump 830 via data interface 895 which may include, for example, one or more of an RF (radio frequency) communication interface/link, a wired data interface such as a USB (universal serial bus) or serial data communication interface or any other suitable data interface for bi-directional data communication between the controller 820 and the pump 830.

As discussed in further detail below, in accordance with embodiments of the present disclosure, architecture to support integration of closed loop control algorithm (whether developed and resident in the PC terminal 810), or integrated into controller 820 are provided. That is, by providing application programming interface (API) to the components of the closed loop system, integration with different control algorithm for implementation as well as testing may be easily achieved with data compatibility and little or no modification to the closed loop control algorithm.

Figure 9:
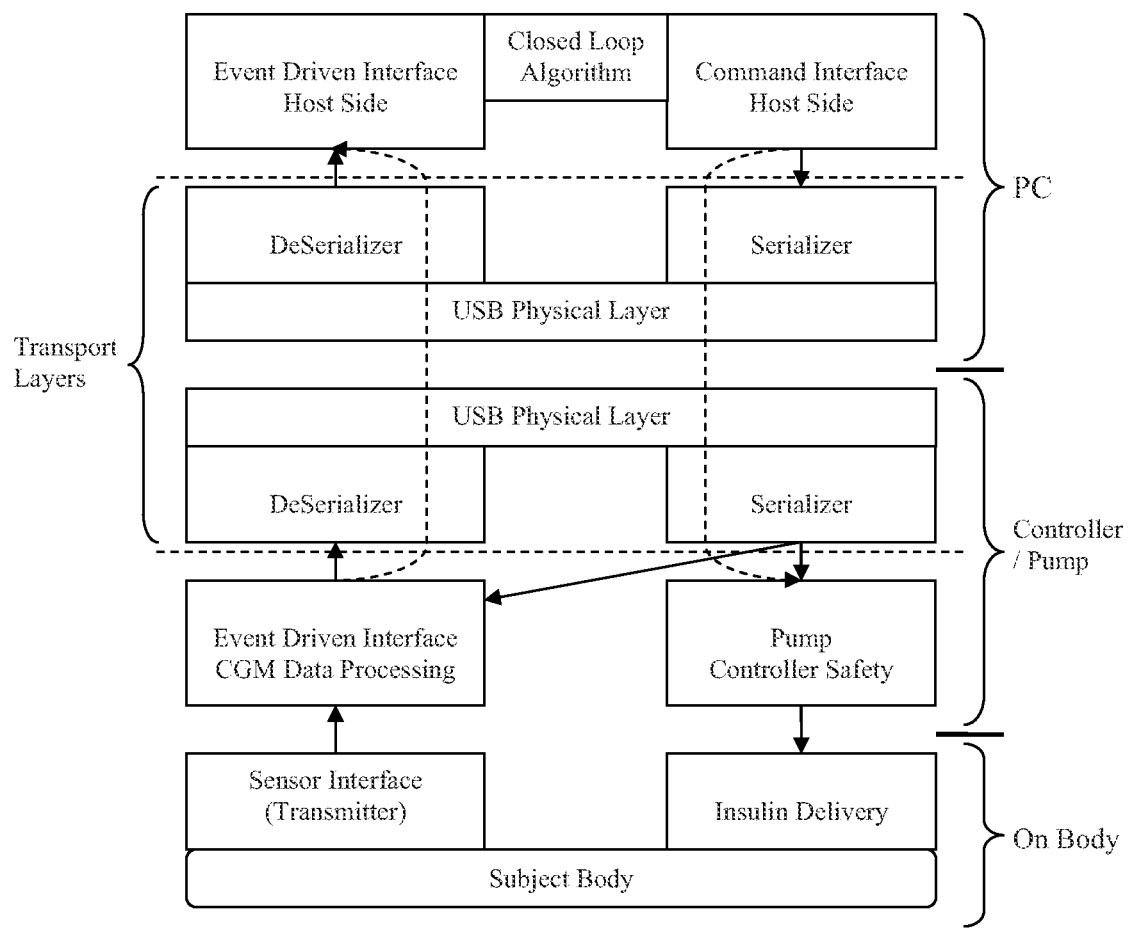
FIG. 9 illustrates an architecture for providing interface to integrate the components of the closed loop system in one aspect.

FIG. 9 illustrates an architecture for providing data/control interface to integrate the components of the closed loop control system in one aspect. Referring to FIG. 9, as can be seen, there is provided transport layers between the controller/pump and the PC terminal. That is, in one embodiment, using the existing USB data ports, data communication may be achieved by serial communication with the PC terminal such that between the devices, an interface layer such as a serializer is provided which encapsulates, for example, the serial commands from the continuous glucose monitoring (CGM) controller to the closed loop algorithm resident in the PC terminal. In one aspect, the serializer may be configured to provide API to execute the necessary and/or desired commands for monitoring and updating the status of the commands.

Referring to FIG. 9, the closed loop algorithm resident in the PC terminal as shown may be configured to call or retrieve for execution/implementation one or more desired functions based, for example, on its internal clock or timer (or programmed or pre-programmed), and in response, triggers or initiates the CGM (continuous glucose monitoring) data processing to serialize the responsive (based on the function call) data which is then provided to corresponding deserializer on the PC terminal via the USB connection. For example, the function call may include a serial command requesting glucose data for the past 10 minutes. The closed loop algorithm may execute this function call to the controller, and in response thereto, the controller may be configured to retrieve the stored glucose data received from the CGM transmitter and provide that information to the deserializer in the PC terminal as a data table, for example.

That is, in one aspect, the application programming interface (API) provided on the controller and the PC terminal are configured to communicate over the data connection (for example, the USB connection) based on serial commands, and thereafter, provided to the closed loop control algorithm for appropriate processing related to control of one or more of the pump parameters or the controller (continuous glucose monitoring) parameters. More specifically, as shown in FIG. 9, the command interface resident in the PC terminal may be configured to generate the appropriate or suitable serial command to implement the desired closed loop control based on the data received from the controller, and thereafter, via the serializer provide the command to the pump and/or the controller over the data connection, which, in one aspect, are configured to deserialize the command for execution and/or implementation.

In this manner, in one aspect, there is provided an interface module which is configured to integrate the closed loop control algorithm with the continuous glucose monitoring system and infusion device that do not require modification to the closed loop control algorithm to provide compatibility and functional integration. For example, in one aspect, serial commands in conjunction with application programming interface (API) are provided to integrate the closed loop system components without changing the closed loop control algorithm. In one aspect, without modifying the interface communication or control, the patient may alter or replace the existing closed loop control algorithm to another algorithm that may be more suited to the patient.

Referring to FIG. 9, while the closed loop control algorithm is shown to reside in the PC terminal, within the scope of the present disclosure, the closed loop control algorithm may be provided in the controller, which, in turn, may be configured for data communication with the pump as well as the sensor interface (transmitter) coupled to an analyte sensor for analyte monitoring. That is, in a further aspect, the PC terminal may be provided as an optional data processing terminal and the closed loop control algorithm may be implemented using the controller device in conjunction with the analyte sensor interface and the pump. This embodiment is further described in detail below in conjunction with FIG. 10.

Figure 10:
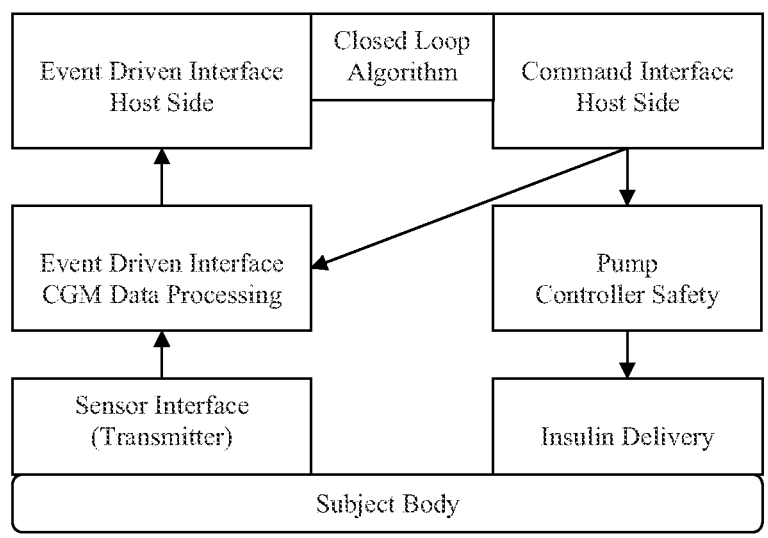
FIG. 10 illustrates an architecture for providing interface to integrate the components of the closed loop system in another aspect.

FIG. 10 illustrates an architecture for providing interface to integrate the components of the closed loop control system in another aspect. As shown, in one aspect, the closed loop control algorithm is integrated in the controller such that the use of the PC terminal with closed loop algorithm may be optional, and the serial commands used may not be necessary. For example, with the application programming interface (API) provided to the controller and the pump, in one aspect, the closed loop control algorithm may be executed based on the data received from the controller related to the real time monitored glucose levels, and in response thereto, provide or issue one or more function calls to command or control the pump and/or the controller to implement the determined command or control based on the executed closed loop control algorithm. As discussed, in accordance with the embodiments of the present disclosure, the defined APIs may be implemented with any closed loop control algorithm and integrated with compatibility.

Within the scope of the present disclosure, other compatible configurations are contemplated in conjunction with a closed loop control system for insulin therapy and diagnosis which are compatible with a variety of closed loop control algorithms without specific modifications to the control algorithms for implementation. In aspects of the present disclosure, the function calls or commands executed or implemented by the one or more APIs include data integrity verification, for example, by including a CRC (cyclic redundancy check) verification such that it may be necessary to verify the checksum of the API command before calling the associated function.

In a further aspect, the defined or programmable APIs may be associated with one or more functions related to the medication delivery profile (e.g., one or more basal delivery profiles, temporary basal profile, delivery rates, delivery duration), delivery profile modification (including, for example, conditions for start/stop of one or more predetermined delivery profiles, conditions defining switching between multiple delivery profiles), safety shut off routine, device (pump and/or controller) operational status monitoring, data processing modes including, for example, batch mode, backup, upload, retrieval, time stamping, logging and the like. Moreover, other compatible APIs are contemplated within the scope of the present disclosure to provide compatibility with multiple closed loop control algorithms and which does not require modification to the algorithms in order to execute or call associated functions or parameters.

In still a further aspect, the defined or programmable APIs may be associated with one or more functions related to the analyte monitoring such as, but not limited to, frequency of analyte data logging, analyte sensor based events such as sensor calibration schedule, modification to the calibration schedule, diagnosis of sensor operation, failure modes related to the analyte sensor, or analyte sensor replacement schedules. In further aspects of the present disclosure, the defined or programmable APIs may be associated with one or more data processing functions from the analyte sensor interface and/or the pump, including, for example, time corresponding the medication delivery profile with the monitored analyte levels, determination or processing of the rate of change information of the monitored analyte levels in conjunction with the medication delivery profile such as the basal profile, monitoring of the temperature (on-skin, body temperature, and the like), for example. In addition, alarm or alert conditions associated with the closed loop control algorithm may be implemented using one or more of the defined or programmable APIs including, for example, but not limited to, occlusion detection in the medication delivery path, rapid rise or decline in the monitored analyte levels, for example.

Accordingly, a method in one aspect includes initiating a programmed function in conjunction with execution of one or more commands related to a closed loop control algorithm, receiving one or more data in response to the one or more commands over a data interface, and executing the one or more commands related to the closed loop control algorithm based on the received one or more data.

The programmed function may be initiated based on an application programming interface function.

The closed loop control algorithm may include closed loop diabetes management algorithm.

In one aspect, the closed loop control algorithm may be configured to modify a delivery profile of a medication.

The closed loop control algorithm may be configured to request a blood glucose value.

The one or more commands in one aspect may include one or more serial commands, where the received one or more data over the interface may be serialized or formatted for serial communication.

The one or more commands may include a command to retrieve one or more of the current or prior monitored analyte level, where the analyte level may include glucose level.

An apparatus in accordance with another embodiment includes a storage unit, and one or more processors coupled to the storage unit, the one or more processors configured to initiate a programmed function in conjunction with execution of one or more commands related to a closed loop control algorithm, to receive one or more data in response to the one or more commands over a data interface; and to execute the one or more commands related to the closed loop control algorithm based on the received one or more data.

A system in accordance with yet another embodiment includes a control unit including a memory unit having stored therein a closed loop control algorithm for execution, and an insulin delivery device in signal communication with the control unit for executing one or more medication delivery functions based on one or more signals received from the control unit, wherein the control unit may include a user interface for initiating one or more application programming interface function associated with one or more of the operation of the insulin delivery device, and further wherein the insulin delivery device may be configured to execute the one or more functions associated with the one or more of the initiated application programming interface functions.

The closed loop control algorithm stored in the memory device of the control unit may include a plurality of closed loop control algorithms.

Various other modifications and alternations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments.

What is claimed is:

1. A method of providing treatment for a medical condition, the method comprising:
   receiving, by a control unit, analyte data, from an analyte sensor in communication with the control unit; and
   controlling, by the control unit, a medication delivery device in accordance with a closed loop control algorithm based on the analyte data, wherein the closed loop control algorithm is associated with a closed loop control operation,
   wherein in controlling the medication delivery device, the control unit is configured to:
      receive a serialized function call from a remote terminal, wherein the serialized function call encapsulates the closed loop control operation in a format that can be processed by the control unit;
      process the serialized function call to identify the closed loop control operation encapsulated in the serialized function call; and
      transmit, to the medication delivery device, a command for executing the closed loop control operation by the medication delivery device.

2. The method of claim 1, wherein controlling the medication delivery device in accordance with the closed loop control algorithm comprises causing the medication delivery device to deliver medication in accordance with the closed loop control algorithm, the method further comprising:
   causing, by the control unit, the medication delivery device to be controlled in accordance with a second closed loop control algorithm instead of the closed loop control algorithm, and wherein controlling the medication delivery device in accordance with the second closed loop control algorithm comprises causing the medication delivery device to deliver medication in accordance with the second closed loop control algorithm.

3. The method of claim 2, wherein causing the medication delivery device to be controlled in accordance with the second closed loop control algorithm instead of the closed loop control algorithm is based on a user action.

4. The method of claim 2, wherein the closed loop control algorithm and the second closed loop control algorithm are stored in a memory accessible by the control unit.

5. The method of claim 2, wherein the second closed loop control algorithm is not modified.

6. The method of claim 1, wherein the closed loop control operation is related to analyte monitoring.

7. The method of claim 1, wherein the analyte data is glucose data and the medication delivery device is an insulin delivery device.

8. The method of claim 1, further comprising:
causing, by the control unit, the medication delivery device to be controlled in accordance with a second closed loop control algorithm instead of the closed loop control algorithm; and
controlling, by the control unit, the medication delivery device in accordance with the second closed loop control algorithm.

9. The method of claim 1, wherein the closed loop control operation is a bolus delivery of insulin.

10. An apparatus comprising:
a control unit; and
a memory including a closed loop control algorithm stored therein, wherein the control unit is configured to:
receive analyte data from an analyte sensor in communication with the control unit;
control a medication delivery device in accordance with the closed loop control algorithm based on the analyte data, wherein the closed loop control algorithm is associated with a closed loop control operation, and wherein in controlling the medication delivery device, the control unit is further configured to:
receive a serialized function call from a remote terminal, wherein the serialized function call encapsulates the closed loop control operation in a format that can be processed by the control unit;
process the serialized function call to identify the closed loop control operation encapsulated in the serialized function call; and
transmit, to the medication delivery device, a command for executing the closed loop control operation by the medication delivery device.

11. The apparatus of claim 10, wherein the control unit is configured to control the medication delivery device in accordance with the closed loop control algorithm by being configured to cause the medication delivery device to deliver medication in accordance with the first closed loop control algorithm, wherein the memory further includes a second closed loop control algorithm, and wherein the control unit is configured to control the medication delivery device in accordance with the second closed loop control algorithm by being configured to cause the medication delivery device to deliver medication in accordance with the second closed loop control algorithm.

12. The apparatus of claim 11, wherein the control unit is configured to cause the medication delivery device to be controlled in accordance with the second closed loop control algorithm instead of the closed loop control algorithm based on a user action.

13. The apparatus of claim 11, wherein the second closed loop control algorithm is not modified.

14. The apparatus of claim 10, wherein the closed loop control operation is related to analyte monitoring.

15. The apparatus of claim 10, wherein the analyte data is glucose data and the medication delivery device is an insulin delivery device.

16. A system comprising:
an analyte sensor configured to generate analyte data;
a medication delivery device;
a control unit; and
a memory including a closed loop control algorithm stored therein, wherein the control unit is configured to:
receive the analyte data generated by the analyte sensor;
control the medication delivery device in accordance with the closed loop control algorithm based on the analyte data, wherein the closed loop control algorithm is associated with a closed loop control operation, and wherein in controlling the medication delivery device, the control unit is further configured to:
receive a serialized function call from a remote terminal, wherein the serialized function call encapsulates the closed loop control operation in a format that can be processed by the control unit;
process the serialized function call to identify the closed loop control operation encapsulated in the serialized function call; and
transmit, to the medication delivery device, a command for executing the closed loop control operation by the medication delivery device.

17. The system of claim 16, wherein the control unit is configured to control the medication delivery device in accordance with the closed loop control algorithm by being configured to cause the medication delivery device to deliver medication in accordance with the closed loop control algorithm, wherein the memory further includes a second closed loop control algorithm, and wherein the control unit is configured to control the medication delivery device in accordance with the second closed loop control algorithm by being configured to cause the medication delivery device to deliver medication in accordance with the second closed loop control algorithm.

18. The system of claim 17, wherein the control unit is configured to cause the medication delivery device to be controlled in accordance with the second closed loop control algorithm instead of the closed loop control algorithm based on a user action.

19. The system of claim 17, wherein the second closed loop control algorithm is not modified.

20. The system of claim 16, wherein the the closed loop control operation is related to analyte monitoring.

21. The system of claim 16, wherein the analyte data is glucose data and the medication delivery device is an insulin delivery device.

* * * * *